United States Patent [19]
Stamler et al.

[11] Patent Number: 5,545,614
[45] Date of Patent: Aug. 13, 1996

[54] CONTROLLING NITROGEN OXIDE CONCENTRATIONS TO MODULATE SKELETAL MUSCLE CONTRACTION

[75] Inventors: Jonathan Stamler, Chapel Hill, N.C.; Lester Kobzik, Needham, Mass.

[73] Assignees: Duke Univ., Durham, N.C.; Harvard College, Cambridge, Mass.

[21] Appl. No.: 349,436

[22] Filed: Dec. 5, 1994

Related U.S. Application Data

[63] Continuation-in-part of Ser. No. 276,105, Jul. 15, 1994.

[51] Int. Cl.$^6$ .................... A61K 38/42; A61K 31/195; A61K 31/22; A61K 31/495
[52] U.S. Cl. .................... 514/6; 514/185; 514/224.8; 514/249; 514/255; 514/551; 514/564
[58] Field of Search .................... 435/190, 191; 514/6, 185, 551, 564, 576, 224.8, 255, 249

[56] References Cited

U.S. PATENT DOCUMENTS

| | | | |
|---|---|---|---|
| 5,028,627 | 7/1991 | Kilbourn et al. | 514/12 |
| 5,039,520 | 8/1991 | Hunter et al. | 514/6 |
| 5,266,594 | 11/1993 | Dawson et al. | 514/560 |
| 5,296,466 | 3/1994 | Kilbourn et al. | 514/6 |
| 5,358,969 | 10/1994 | Williamson et al. | 514/632 |
| 5,449,688 | 9/1995 | Wahl et al. | 514/546 |

OTHER PUBLICATIONS

J. Pharmacology and Experimental Therapeutics, vol. 254, No. 3, issued 1990, Wolin et al, "Methylene Blue Inhibits Vasodilation . . . ", pp. 872–876.
Pediatric Research, vol. 35 (4 Part 2), issued Apr. 1994, Williams et al, "Induction And Characterization of Inducible . . . ", p. 61A, abstract No. 350.

*Primary Examiner*—Jeffrey E. Russel
*Attorney, Agent, or Firm*—Charles J. Herron; Elliot M. Olstein

[57] ABSTRACT

A method for inhibiting or relaxing skeletal muscle contractions and for treating disease states resulting from or exacerbated by undesirable skeletal muscle contractions by administering a skeletal muscle relaxing amount of nitroxyl ion($NO^-$), nitrosonium ion($NO^+$), nitric oxide and nitric oxide adducts or providers. A process for stimulating, improving or enhancing muscle contraction in a mammal by treating the mammal with an effective amount of (i) a nitric oxide synthase inhibitor or (ii) a nitric oxide scavenger.

7 Claims, 5 Drawing Sheets

CONTROLLING NITROGEN OXIDE CONCENTRATIONS TO MODULATE SKELETAL MUSCLE CONTRACTION

This application is a continuation-in-part of U.S. Ser. No. 08/276,105, filed Jul. 15, 1994, (pending).

Nitric oxide (NO) is an important endogenous modulator of smooth muscle function (Ignarro, *FASEB J.*, Vol. 3, pgs. 31–36 (1989); Moncada, Palmer, et al., *Pharmcol. Rev.*, Vol. 43, pg. 109 (1991)). NO activates a cGMP dependent mechanism to inhibit Ca++ release from internal stores, and thereby depress smooth muscle contraction (Schmidt, Lohmann, et al., *Biochem. Biophys. Acta*, Vol. 1178, pgs. 153–175 (1993)). In contrast to expanding data about the effects of NO in smooth muscle, relatively little is known about the role of NO or cyclic nucleotides in skeletal muscle function.

In one aspect the present invention provides a process for relaxing or inhibiting the contraction of skeletal muscle of a mammal, particularly a human, by treating the mammal with an effective amount of nitric oxide. This encompasses the use of nitric oxide species, particularly for example nitroxyl ion (NO$^-$), nitrosonium ion (NO$^+$), and uncharged nitric oxide, which can be provided by gaseous nitric oxide and/or nitric oxide adducts or providers in the treatment of disease states. Such disease states may be those which result from or are exacerbated by undesirable contractions of skeletal muscle, such as, for example, spastic muscle disease. Such nitric oxide species also may be employed in the treatment of muscle spasms.

In particular, this aspect of the invention is directed to a method for relaxing skeletal muscle by administering a therapeutically effective amount of one or more of the compounds identified herein (particularly an S-nitrosothiol compound) to an animal, particularly a human.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide(NO●) and charged nitric oxide species, particularly including nitrosonium ion(NO$^+$) and nitroxyl ion(NO$^-$). The nitric oxide releasing, delivering, or transferring compounds, having the structure X-NO, include any and all such compounds which provide nitric oxide to its intended site of action in a form active for their intended purpose. As used here, the term "NO adducts" encompasses any of such nitric oxide releasing, delivering or transferring compounds.

One group of such NO adducts is the S-nitrosothiols, which are compounds that include at least one —S—NO group. Such compounds include S-nitroso-polypeptides(the term "polypeptide is contemplated to include proteins and also polyamino acids that do not possess an ascertained biological function, and derivatives thereof), S-nitrosylated amino acids(including natural and synthetic amino acids and their stereoisomers and racemic mixtures and derivatives thereof), S-nitrosated sugars, S-nitrosated oligonucleotides and derivatives thereof (preferably of at least 5, and more particularly 5–200, nucleotides), S-nitrosated hydrocarbons where the hydrocarbon can be a branched or unbranched, saturated or unsaturated aliphatic hydrocarbon, or an aromatic hydrocarbon, S-nitroso hydrocarbons having one or more substituent groups in addition to the S-nitroso group, and heterocyclic compounds. S-nitrosothiols and the methods for preparing them are described in U.S. Pat. No. 5,380,758, filed Sep. 14, 1992, Oae et al., Org. Prep. Proc. Int., 15(3):165–198 (1983); Loscalzo et al., J. Pharmacol. Exp. Ther., 249(3):726729 (1989) and Kowaluk et al., J. Pharmacol. Exp. Ther., 256: 1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins(where the NO group is attached to one or more sulfur groups on an amino acid or amino acid derivative) from various functional classes including enzymes, such as tissue-type plasminogen activator (TPA) and cathepsin B; transport proteins, such as lipoproteins, heme proteins such as hemoglobin and serum albumin; and biologically active proteins, such as the immunoglobulins and the cytokines. Such nitrosylated proteins are described in PCT Published Application No. WO 93/09806, published May 27, 1993.

Further examples of suitable S-nitrosothiols include those having the structures:

$$CH_3(CH_2)_xSNO \qquad (i)$$

wherein x equals 2 to 20;

$$HS(CH_2)_xSNO \qquad (ii)$$

wherein x equals 2 to 20; and

$$ONS(CH_2)_xY \qquad (iii)$$

wherein x equals 2 to 20 and Y is selected from the group consisting of fluoro, C$_1$-C$_6$ alkoxy, cyano, carboxamido, C$_3$-C$_6$ cycloalkyl, aralkoxy, C$_2$-C$_6$ alkylsulfinyl, arylthio, C$_1$-C$_6$ alkylamino, C$_2$-C$_{15}$ dialkylamino, hydroxy, carbamoyl, C$_1$-C$_6$ N-alkylcarbamoyl, C$_2$-C$_{15}$ N,N-dialkylcarbamoyl, amino, hydroxyl, carboxyl, hydrogen, nitro and aryl; wherein aryl includes benzyl, naphthyl, and anthracenyl groups.

Other suitable S-nitrosothiols that are S-nitroso-angiotensin converting enzyme inhibitors (hereinafter referred to as S-nitroso-ACE inhibitors) are described in Loscalzo, U.S. Pat. No. 5,002,964 (1991) and Loscalzo et al., U.S. Pat. No. 5,025,001 (1991) both of which are incorporated in their entirety by reference. Examples of such S-nitroso-ACE inhibitors include compounds having structure (1):

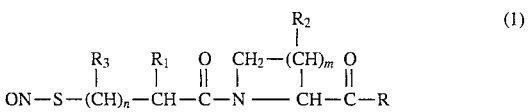

wherein

R is hydroxy, NH$_2$, NHR$^4$, NR$^4$R$^5$, or C$_1$-C$_7$ alkoxy, wherein R$^4$ and R$^5$ are C$_1$-C$_4$ alkyl, or phenyl, or C$_1$-C$_4$ alkyl substituted by phenyl;

R$^1$ is hydrogen, C$_1$-C$_7$ alkyl, or C$_1$-C$_7$ alkyl substituted by phenyl, amino, guanidino, NHR$^6$, NR$^6$R$^7$, wherein R$^6$ and R$^7$ are methyl or C$_1$-C$_4$ alkanoyl;

R$^2$ is hydrogen, hydroxy, C$_1$-C$_4$ alkoxy, phenoxy, or C$_1$-C$_7$ alkyl;

R$^3$ is hydrogen, C$_1$-C$_4$ or C$_1$-C$_7$ alkyl substituted by phenyl;

m is 1 to 3; and n is 0 to 2.

Other suitable S-nitroso-ACE inhibitors include N-acetyl-S-nitroso-D-cysteinyl-L-proline, N-acetyl-S-nitroso-D,L-cysteinyl-L-proline, 1-(4-amino-2-S-nitroso)mercaptomethyl butanoyl)-L-proline, 1-[5-guanidino-2-(S-nitroso)mercaptomethyl-pentanoyl] -L-proline, 1-[5-amino-2-(S-nitroso) mercaptomethyl-pentanoyl]-4-hydroxy-L-proline, 1-[5-guanidino-2-(S-nitroso)mercaptomethyl-pentanoyl]-4-hydroxy-L-proline, 1-[2-aminomethyl-3(S-nitroso)-mercaptomethyl-pentanoyl]-L-proline, and S-nitroso-L-cysteinyl-L-proline.

Additional suitable S-nitroso-ACE inhibitors include those having structures (2–3):

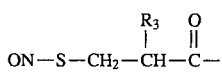

(2)

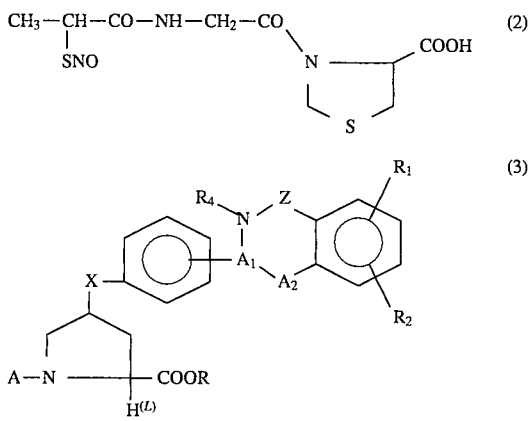

(3)

wherein

X is oxygen or sulfur;

$A_1-A_2-$ is CH—NH or —C=N—;

A is

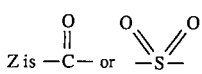

R is selected from hydrogen, lower ($C_1$–$C_4$) alkyl, benzyl, benzhydryl, and salt forming ion;

$R_1$ and $R_2$ are independently selected from hydrogen, halogen, lower alkyl, lower alkoxy, halo substituted lower alkyl, nitro, and $SO_2NH_2$;

Z is $-\overset{O}{\overset{\|}{C}}-$ or $-\overset{O}{\underset{O}{\overset{\|}{\underset{\|}{S}}}}-$ $R_3$ is hydrogen, lower alkyl, halo substituted lower alkyl, phenyl, benzyl, phenethyl, or cycloalkyl; and $R_4$ is hydrogen, lower alkyl, halo substituted lower alkyl, hydroxy substituted lower alkyl, —$(CH_2)_q$—N (lower alkyl)$_2$ or —$(CH_2)_q$—$NH_2$ and q is one, two, three or four.

Additional suitable compounds include those having structures (4–11):

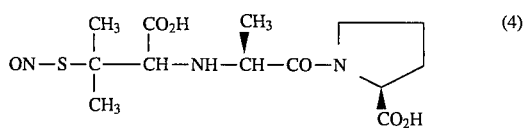

(4)

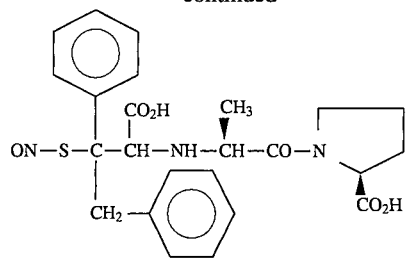

(5)

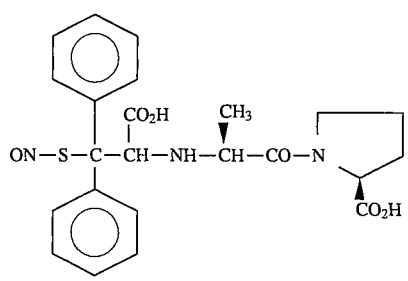

(6)

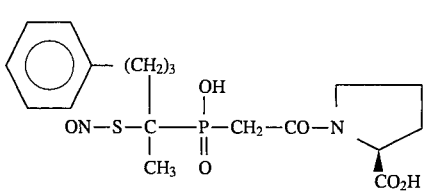

(7)

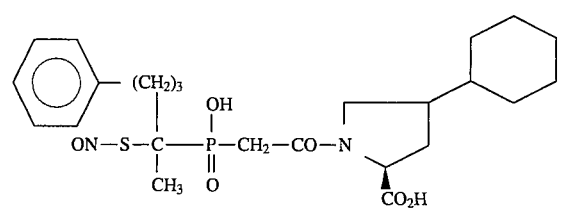

(8)

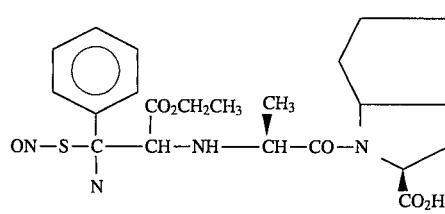

(9)

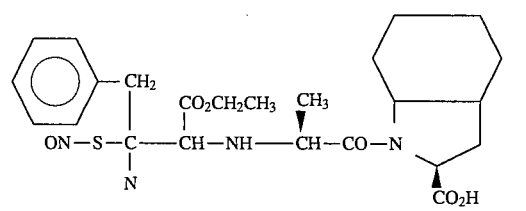

(10)

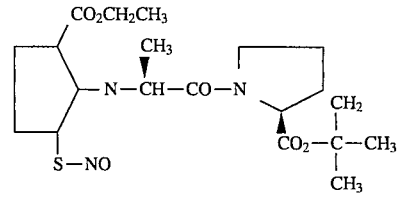

(11)

The S-nitroso-ACE inhibitors can be prepared by various methods of synthesis. In general, the thiol precursor is prepared first, then converted to the S-nitrosothiol derivative by nitrosation of the thiol group with $NaNO_2$ under acidic conditions (pH=1 to 5) which yields the S-nitroso derivative. Acids which may be used for this purpose include aqueous sulfuric, acetic and hydrochloric acids. Thiol precursors are prepared as described in the following: U.S. Pat. Nos. 4,046,889 (1977); 4,052,511; 4,053,651; 4,113,751, 4,154, 840, 4,129,571 (1978), and 4,154,960 (1979) to Ondetti et al.; U.S. Pat. No. 4,626,545 (1986) to Taub; and U.S. Pat. Nos. 4,692,458 (1987) and 4,692,459 (1987) to Ryan et al., Quadro, U.S. Pat. No. 4,447,419 (1984); Haugwitz et al.; U.S. Pat. No. 4,681,886 (1987), Bush et al., U.S. Pat. No. 4,568,675 (1986), Bennion et al., U.S. Pat. No. 4,748,160 (1988), Portlock, U.S. Pat. No. 4,461,896 (1984), Hoefle et al., European Patent Application Publication No. 0 088 341 (1983), Huange et al., U.S. Pat. No. 4,585,758 (1986), European Patent application Publication No. 0 237 239, European Patent application Publication No. 0 174 162, published in 1986, European Patent application Publication No. 0 257 485, published in 1988, all of which are incorporated by reference herein.

Another group of such NO adducts are compounds that include at least one —O—NO group. Such compounds include O-nitroso-polypeptides (the term "polypeptide" includes proteins and also polyamino acids that do not possess an ascertained biological function, and derivatives thereof); O-nitrosylated amino acids (including natural and synthetic amino acids and their stereoisomers and racemic mixtures and derivatives thereof); O-nitrosated sugars; O-nitrosated-modified and unmodified oligonucleotides (preferably of at least 5, and more particularly 5–200, nucleotides); O-nitrosated hydrocarbons where the hydrocarbon can be a branched or unbranched, saturated or unsaturated aliphatic hydrocarbon, or an aromatic hydrocarbon; O-nitroso hydrocarbons having one or more substituent groups in addition to the O-nitroso group; and heterocyclic compounds.

Another group of such NO adducts is the N-nitrosoamines, which are compounds that include at least one —N—NO group. Such compounds include N-nitroso-polypeptides (the term "polypeptide" includes proteins and also polyamino acids that do not possess an ascertained biological function, and derivatives thereof); N-nitrosylated amino acids (including natural and synthetic amino acids and their stereoisomers and racemic mixtures); N-nitrosated sugars, N-nitrosated-modified and unmodified oligonucleotides (preferably of at least 5, and more particularly 5–200, nucleotides); N-nitrosated hydrocarbons where the hydrocarbon can be a branched or unbranched, saturated or unsaturated aliphatic hydrocarbon, or an aromatic hydrocarbon; N-nitroso hydrocarbons having one or more substituent groups in addition to the N-nitroso group; and heterocyclic compounds.

Another group of such NO adducts is the C-nitroso compounds that include at least one —C—NO group. Such compounds include C-nitroso-polypeptides (the term "polypeptide" includes proteins and also polyamino acids that do not possess an ascertained biological function and derivatives thereof); C-nitrosylated amino acids (including natural and synthetic amino acids and their stereoisomers and racemic mixtures); C-nitrosated sugars; C-nitrosated-modified and unmodified oligonucleotides (preferably of at least 5, and more particularly 5–200, nucleotides); C-nitrosated hydrocarbons where the hydrocarbon can be a branched or unbranched, saturated or unsaturated, aliphatic hydrocarbon, or an aromatic hydrocarbon; C-nitroso hydrocarbons having one or more substituent groups in addition to the C-nitroso group; and heterocyclic compounds. A representative example is P-nitrosotyrosine.

Another group of such NO adducts is the nitrates which have at least one —O—$NO_2$ group. Such compounds include O-nitroso-polypeptides (the term "polypeptide" includes proteins and also polyamino acids that do not possess an ascertained biological function, and derivatives thereof); amino acids (including natural and synthetic amino acids and their stereoisomers and racemic mixtures, and derivatives thereof); sugars; modified and unmodified oligonucleotides (preferably of at least 5, and more particularly 5–200, nucleotides); hydrocarbons where the hydrocarbon can be a branched or unbranched, saturated, or unsaturated aliphatic hydrocarbon, or an aromatic hydrocarbon; hydrocarbons having one or more substituent groups; and heterocyclic compounds. A preferred example is nitroglycerin.

Another group of such NO adducts is the nitroso-metal compounds which have the structure $(R)_n$-A-M-$(NO)_x$. R includes polypeptides (the term "polypeptide" to includes proteins and also polyamino acids that do not possess an ascertained biological function and derivatives thereof); amino acids(including natural and synthetic amino acids and their stereoisomers and racemic mixtures and derivatives thereof); sugars; modified and unmodified oligonucleotides (preferably of at least 5, and more particularly 5–200, nucleotides); hydrocarbons where the hydrocarbon can be a branched or unbranched and saturated or unsaturated aliphatic hydrocarbon, or an aromatic hydrocarbon; hydrocarbons having one or more substituent groups in addition to the A-nitroso group, and heterocyclic compounds. A is S, O, or N, n and x are each integers independently selected from 1, 2 and 3, and M is a metal, preferably a transition metal. Preferred metals include iron, copper, manganese, cobalt, selenium and lithium. Also contemplated are N-nitrosylated metal centers such as nitroprusside.

Another group of such NO adducts are the N-oxo-N-nitrosoamines which have an R—N($O^-M+$ )—NO or an R—NO—NO— group. R includes polypeptides (the term "polypeptide" includes proteins and also polyamino acids that do not possess an ascertained biological function, and derivatives thereof); amino acids(including natural and synthetic amino acids and their stereoisomers and racemic mixtures and derivatives thereof); sugars; modified and unmodified oligonucleotides(preferably of at least 5, and more particularly 5–200, nucleotides); and hydrocarbons where the hydrocarbon can be a branched or unbranched, saturated or unsaturated aliphatic hydrocarbon, or an aromatic hydrocarbon; hydrocarbons having one or more substituent groups; and heterocyclic compounds. R is preferably a nucleophilic (basic) moiety. M+ is a metal cation, such as, for example, a Group I metal cation. As representative examples, there may be mentioned N-hydroxy-nitrosoamines produced from alkylene amines such as diethylamine; spermine, etc.

Another group of such NO adducts is the thionitrates which have the structure R—$(S)_x$—NO wherein x is an integer of at least 2. R is as described above for the S-nitrosothiols. Preferred are the dithiols wherein x is 2.

The invention is also directed to the use of gaseous nitric oxide or nitric oxide releasing compounds to alleviate skeletal muscle contraction and spasm, and thus facilitate procedures involving diagnostic instrumentation such as endoscopy of the upper esophagus.

An additional embodiment of the invention relates to the administration of a compound which provides nitric oxide as part of a pharmaceutical composition, comprising a pharmaceutically acceptable carrier, to achieve the physiological effects discussed above.

The pharmaceutical compositions utilized in this invention can be administered by intranasal, oral, enteral, topical, vaginal, sublingual, rectal, intramuscular, intravenous, or subcutaneous means.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable vehicles consist of solutions, preferably oily or aqueous solutions, as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect. In general, the compound is administered in an amount which achieves a serum concentration of the compound of from about 1 nM to about 1 mM.

The above compounds also may be employed in alleviating or reversing muscle fatigue. One of the indications associated with muscle fatigue is the overproduction of superoxide. The administration of superoxide dismutase, which inactivates superoxide, ameliorates or reverses muscle fatigue and improves muscle force. Superoxide dismutase, when administered to an individual suffering from muscle fatigue, also improves muscle contraction. (Reid, et al., *J. Appl. Physiol.*, Vol. 73, pg. 1797 (1992)). Nitric oxide, however, provides for increased inactivation of superoxide as compared with superoxide dismutase. Thus, in accordance with another aspect of the present invention, there is provided a method of alleviating or reversing muscle fatigue in a mammal comprising administering to a mammal an effective muscle fatigue alleviating or reversing amount of nitric oxide. The nitric oxide may be in the forms of the compounds and species hereinabove described. The nitric oxide may be administered in combination with pharmaceutical carriers and in dosages such as those hereinabove described.

In accordance with another aspect of the present invention, there is a provided a method for stimulating the contraction of muscles (such as, for example, skeletal muscles) of a mammal by treating the mammal with an effective amount of a nitric oxide synthase (or NOS) inhibitor.

Suitable nitric oxide synthase inhibitors which may be employed include, but are not limited to, arginine-based analogues such as $N^G$-mono-methyl-L-arginine (NMA), nitro-arginine, N-nitro-L-arginine methyl ester, N-amino-L-arginine, and N-methyl-L-arginine; flavoprotein binders such as diphenylene iodonium and related iodonium derivatives, ornithine and ornithine derivatives such as N-iminoethyl-L-ornithine; redox dyes such as methylene blue; calmodulin binders such as trifluoropiperazine and calcinarin; heme binders; and depleters of biopterin such as methotrexate.

Such nitric oxide synthase inhibitors are useful particularly in the treatment of neuromuscular diseases and other diseases characterized by the impairment of the ability of muscles to contract. Such diseases include, but are not limited to, amyotrophic lateral sclerosis (Lou Gehrig's disease), the muscular dystrophies, congestive heart failure, lung diseases, and other diseases characterized by the impairment of muscle function.

Another aspect of the invention provides a process for stimulating, improving or enhancing muscle contraction by contacting the muscle with an effective amount of a nitric oxide scavenger. Preferably the nitric oxide scavenger is a heme-containing compound. The heme-containing compound can be any molecule containing chelate complex of protoporphyrin with Fe(II), and is most preferably a heme-containing protein or polypeptide such as hemoglobin or myoglobin.

Such nitric oxide scavenger compounds are useful particularly in the treatment of neuromuscular diseases and other diseases characterized by the impairment of the ability of muscles to contract. Such diseases include, but are not limited to, amyotrophic lateral sclerosis (Lou Gehrig's disease), the muscular dystrophies, congestive heart failure, lung diseases, and other diseases characterized by the impairment of muscle function.

The above compounds may be combined with pharmaceutical carriers as hereinabove described for administration to a mammalian host (which may be a human or non-human host) and in dosages such as to achieve a serum concentration of the compound of from about 1 nM to about 1 mM.

The invention will now be described with respect to the drawings.

In arriving at the present invention the inventors investigated the production, source and function of NO in mammalian skeletal muscle and made several important new observations, including the following.

Without further elaboration, it is believed that one skilled in the art can, using the preceding description, utilize the present invention to its fullest extent. The following examples are, therefore, to be construed as merely illustrative, and not limitative of the disclosure in any way whatsoever.

The entire text of all publications cited above and below are hereby incorporated by reference.

EXAMPLE 1

Skeletal Muscle Contains Active NOS Enzyme

Biochemical assay of skeletal muscle homogenates showed clear bNOS activity, as measured by conversion of radiolabelled arginine to citrulline, as shown in Table 1.

Rat lower limb muscles, diaphragm, heart and cerebellum were dissected after euthanasia. NO synthase activity was measured by monitoring the conversion of $^3$H-arginine to $^3$H-citrulline. Tissues were homogenized in 40 volumes of homogenization buffer containing 25 mM Tris-HCl (pH 7.4) and 1mM EDTA. The homogenate was centrifuged at 4° C. for 15 min at 20,000Xg. The pellet was resuspended in half the original volume of homogenization buffer. 25 uL of homogenate was added to 25 uL of 100 nM $^3$H- arginine (50 Ci/mmole) and 100 uL of assay buffer containing 50 mM Hepes (pH 7.4), 1 mM NADPH, 1mM EDTA and 1.25 mM $CaCl_2$. After incubation for 15 min at 22° C., assays were terminated with 2 ml of 20 mM Hepes (pH 5.5), 2 mM EDTA. Samples were applied to 1 ml columns of Dowex Ag5Ovvx-8 (Na+-form) which were eluted with 2 ml of water. $^3$H-citrulline was quantified by liquid scintillation spectroscopy of the 4 ml flow through. Results of two separate experiments are shown in Table 1 below.

TABLE 1

| Tissue | NOS Activity (pmols/min/mg protein) | |
|---|---|---|
|  | expt. 1 | expt. 2 |
| Cerebellum | 145 | 158 |
| Ext. Digitorum Longus | 13.5 | 13.7 |
| Gastrocnemius | 11 | 12 |
| Plantaris | 14 | 9.5 |
| Diaphragm | 5.2 | 5.0 |
| Soleus | 2.5 | 2.5 |
| Heart | 0.9 | 1.3 |

The NOS was associated with the membrane fraction of the homogenate samples, consistent with immunolocalization results described below. Western staining with anti-b-NOS identified an immunoreactive band of the predicted molecular weight which co-migrated with NOS from rat cerebellum (Mr=160kDa, not shown).

EXAMPLE 2

Skeletal Muscle b-NOS is Localized to Type II Fibers

Figure 1:
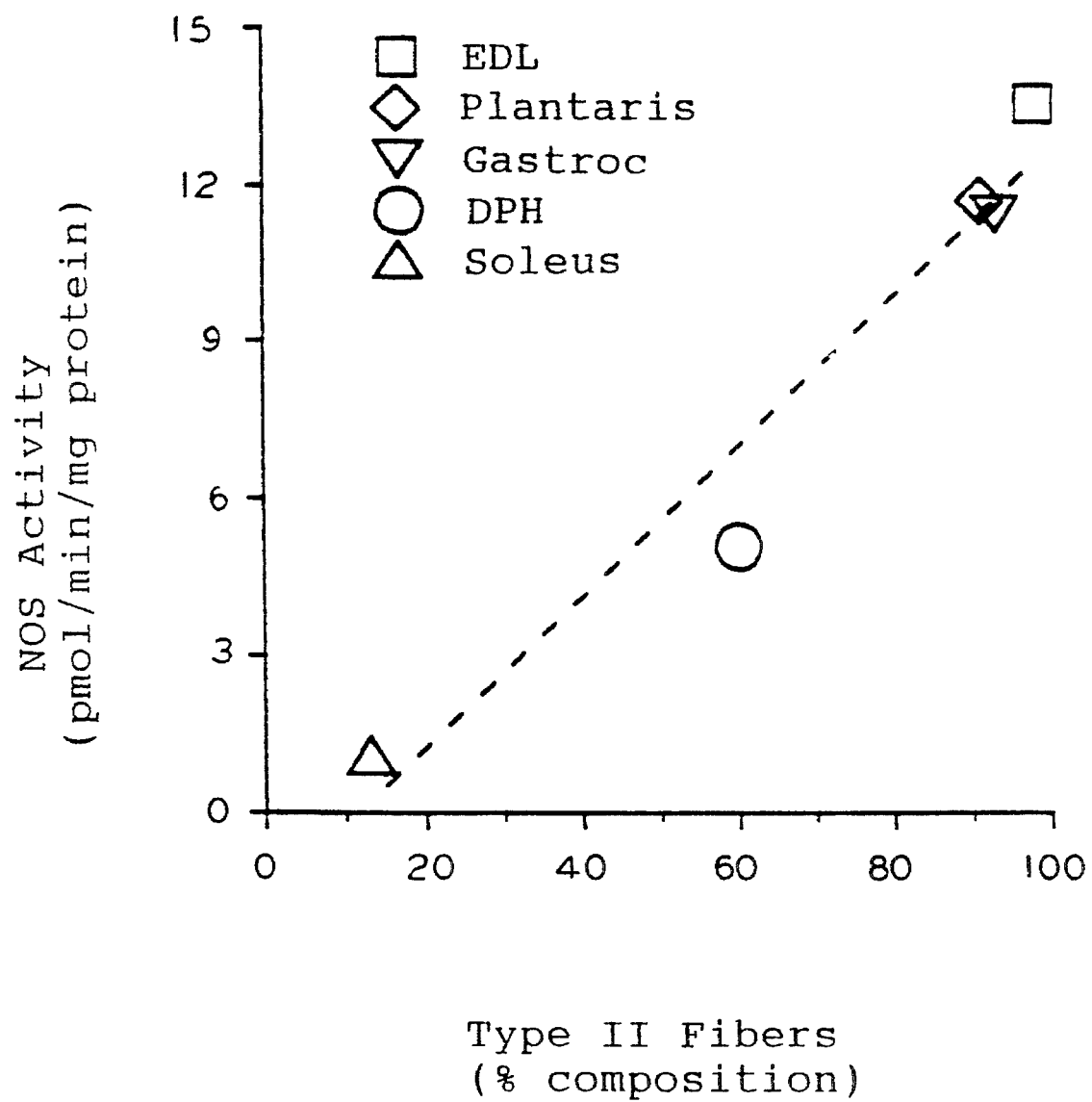
FIG. 1. Skeletal muscle NOS activity is related to the proportion of type II fibers Average NOS activities (Table 1) measured in extensor digitorum longus (EDL), plantaris, gastrocnemius (Gastroc), diaphragm (DPH), and soleus are plotted as a function of published values for type II composition. (Armstrong, et al., *Am. J. Anat.*, Vol. 171, pg. 259 (1984); Metzger, et al., *J. Appl. Physiol.*, Vol. 58, pg. 1085 (1985)). These data were strongly correlated ($r=0.97$; $p<0.001$); a dashed line depicts the regression equation ($y=0.144x-1.63$).
Figure 2B:
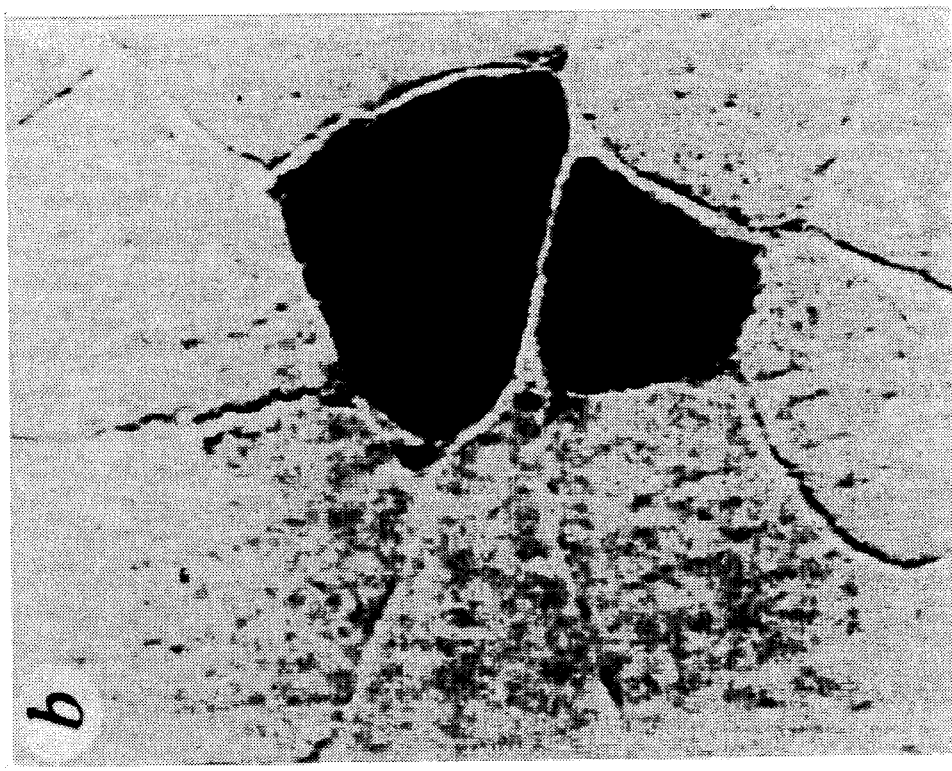
FIGS. 2A and 2B. NOS antigen is localized to skeletal muscle type II fiber membranes. A) Immunohistochemical labeling (performed as previously described (Kobzik, et al., *Am. J. Respir. Cell. Mol. Biol.*, Vol. 9, pg. 371 (1993); Bredt, et al., *Nature*, Vol. 347, pg. 768 (1990)) of cryostat sections of rat skeletal muscle showed distinct labeling of muscle fiber surface membrane in many but not all fibers (note negative fibers in center). Controls including irrelevant primary antibody or buffer showed no labeling (not shown). B) Histochemical staining of adjacent serial sections for ATPase identified NOS- negative fibers as type I fibers. A standard histochemical protocol was followed (Vacca, *Laboratory Manual of Cytochemistry*, Raven Press, New York (1985)), including preincubation of sections at pH 9.4, 4.6 and 4.2 to optimize differentiation of muscle types. The results illustrated are from a sample preincubated at pH 4.2 which results in intense labeling of type I fibers only. (A&B, 400× original magnification).
Figure 2A:
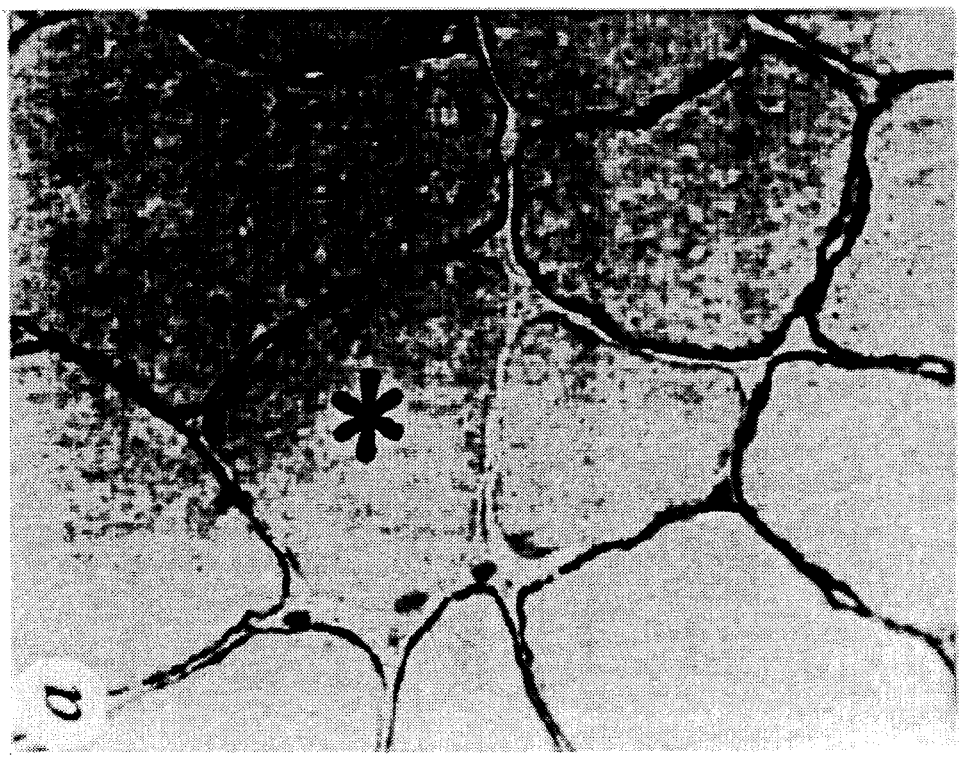

When the NOS activities of individual muscles were plotted against their % composition by type II fibers (Armstrong, et al., 1984 Metzger, et al., 1985), a striking correlation (r=0.974) was found (FIG. 1). Immunohistochemical localization with antibody specific for B-NOS (Bredt, et al., 1990) showed prominent NOS antigen in the membranes of skeletal muscle fibers (FIG. 2A). Interestingly, some fibers in all muscles examined were negative (FIG. 2A). Using histochemical stains for ATPase on adjacent serial sections, these NOS-negative fibers were identified as type I or slow fibers. Since muscles vary in their relative proportion of type I and II fibers (Pette, et al. *Rev. Physiol. Biochem. Pharmacol.*, Vol. 116, pg. 1 (1990)), these findings are consistent with the observations illustrated in FIG. 1 that NOS biochemical activity increases as the proportion of type I (NOS-negative fibers by immunocytochemistry) decreases (Pette, et al., 1990).

EXAMPLE 3

Skeletal Muscle Contractile Properties are Related to NOS Activity

Figure 3A:
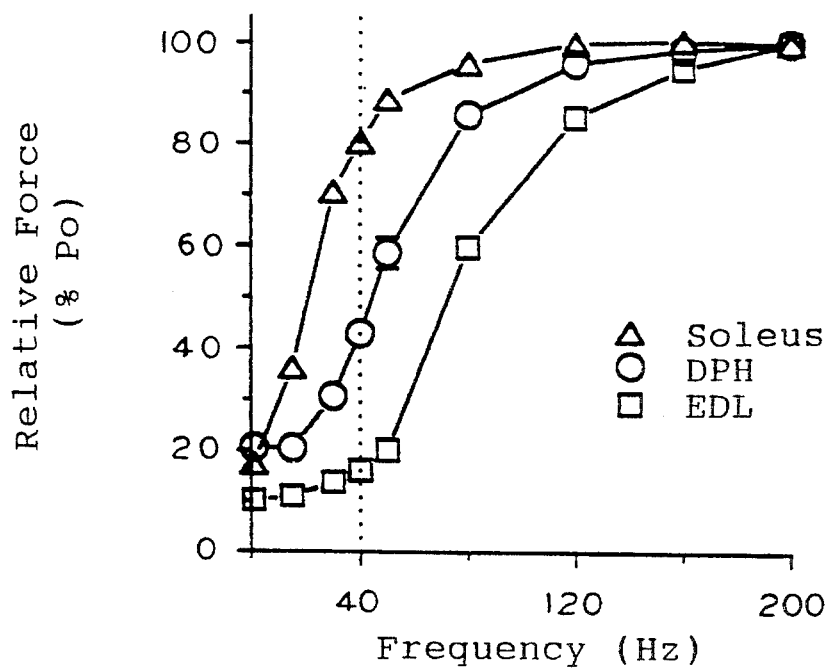
FIGS. 3A and 3B. Skeletal muscle contractile properties are related to NOS activity Muscles (Soleus, n=6; DPH, diaphragm fiber bundles, n=7; EDL, extensor digitorum longus, n=5) were surgically isolated from deeply anesthetized rats, mounted in vitro at optimal length, and incubated at 37° C. in oxygenated buffered Krebs-Ringer solution containing d-tubocurarine 25 uM. Direct field stimulation (0.2 ms pulses, 250 ms train duration, supramaximal voltage) was used to evoke twitch (1 Hz) and tetanic (15, 30, 40, 50, 80, 120, 200 Hz) contractions. Isometric force was measured. Upper panel (A) depicts the average forces (±SE) developed at frequencies of 1–200 Hz. Tetanic stimulation at any submaximal frequency (15–150 Hz) evoked different amounts of force production among the muscles (Soleus>DPH>EDL). A vertical dotted line identifies the frequency (40 Hz) used in comparisons of NOS activity. Lower panel (B) shows the relative forces developed by individual muscles at 40 Hz (data points depict individual experiments) as a function of NOS activity (averages of expts. #1 and 2, Table 1). Contractile responses exhibited a strong, negative correlation (r=0.92; p<0.001) with NOS activity; a dashed line depicts the regression equation (y=−5.13×+82.7).
Figure 3B:
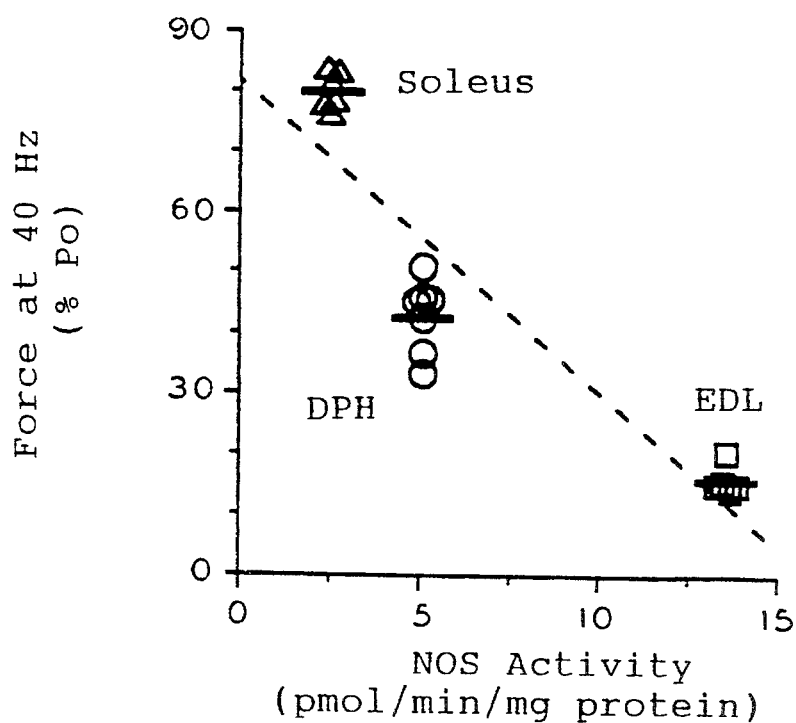

Contractile properties of muscles that span the range of fiber type and NOS activity shown in FIG. 1 were measured. Among soleus, diaphragm and extensor digitorum longus (EDL), position of the stress-frequency relationship was shifted to the right as NOS activity increased (FIG. 3).

The functional role of NO using fiber bundles isolated from diaphragm, a muscle with intermediate biochemical NOS activity (Table 1), fiber composition (FIG. 1), and contractile properties (FIG. 3), then was examined. The diaphragm is also relevant to recent therapeutic interventions with NO for respiratory diseases (Frostell, et al., *Circulation*, Vol. 83, pg. 2038 (1991)).

EXAMPLE 4

Endogenous NO Depresses Contractile Function of Skeletal Muscle

Figure 4A:
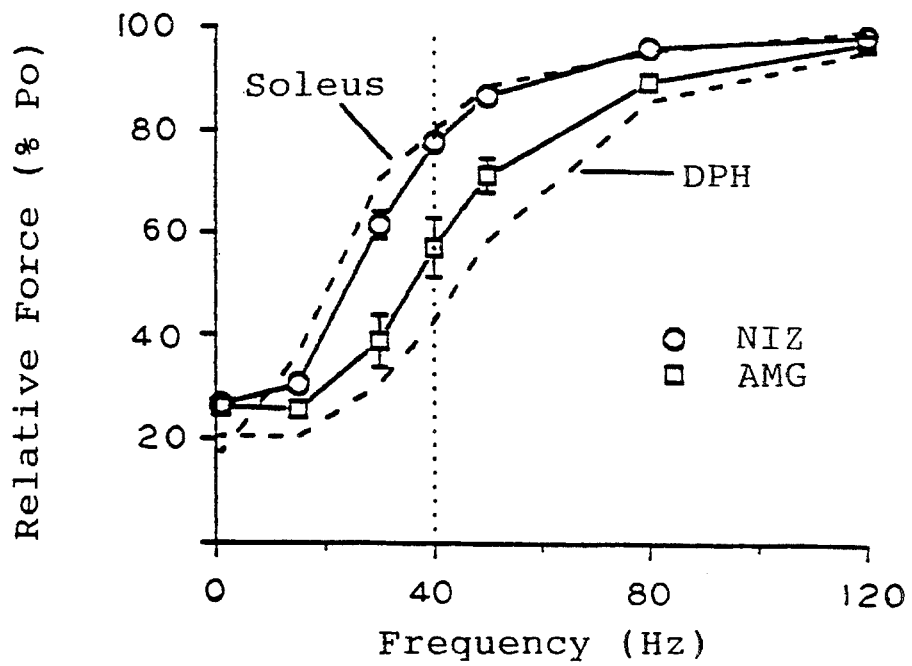
FIGS. 4A and 4B. Endogenous NO depresses contractile function. Fiber bundles were isolated from rat diaphragm and studied using methods described in FIG. 3. Panel A depicts the average forces (±SE) developed at stimulus frequencies of 1–120 Hz by muscles incubated in Krebs-Ringer solution containing either 7-nitroindazole (NIZ; n=3 per frequency) or aminoguanidine (AMG, n=3 per frequency). Forces are expressed as percentages of maximal tetanic force (PO). NIZ 1mM shifted the diaphragm force-frequency relationship up and to the left (p<0.0001 by repeated measures ANOVA) such that it was indistinguishable from the relationship measured in untreated soleus (upper dashed curve; transcribed from FIG. 3). Similar shifts of lesser magnitude were produced by AMG 1mM (p<0.05) and by NLA 1mM (p<0.05, data not shown). In subsequent studies, pharmacologic effects were tested using 40 Hz stimulations, based on the force-frequency relationships shown in A. Panel B shows the forces developed at 40 Hz by fiber bundles (n=5 or 6/group) treated with S-nitroso-N-acetylcysteine (SNAC; exogenous NO donor) 100 uM, nitroprusside (NP; NO donor) 100 uM, nitro-L-arginine (NLA; NOS inhibitor) 10 mM, NLA plus SNAC, or NLA plus NP. Forces are expressed as percentages of the average force developed at 40 Hz by time- and stimulus-matched control muscle (shown ±SE by horizontal lines). *=significantly different from all other groups (p<0.0001); SNAC and NLA+NP were not different from control.

Three specific NOS inhibitors were used to assess the role of endogenous NO on contractile function. Each shifted the forcefrequency relationship leftward. Significant effects were seen with 100 uM 7-nitroindozole (NIZ), a b-NOS specific inhibitor (Moore, et al., *Br. J. Pharmacol.*, Vol. 108, pg. 296 (1993)) ($p<0.05$). At 1mM NIZ profoundly influenced contractile function, causing the diaphragm forcefrequency curve to closely approximate that of the soleus (a slow-twitch postural muscle) (FIG. 4A). Similar, albeit smaller, contractile increases were seen with aminoguanidine (AMG, FIG. 4A) and nitro-L-arginine (Nathan, *FASEB J.*, Vol. 6, pg. 305 (1992)) (NLA) over the same dose range, but not with L-arginine. The lesser potency of AMG is compatible with its relative selectivity towards other NOS isoforms (Misko, et al., *Eur. S. Pharmacol.*, Vol. 233, pg. 119 (1993)). The limitation of NIA, an arginine-based inhibitor, (as compared to NIZ) may be explained by the high intracellular concentrations of arginine in skeletal muscle, known to be in the mM range (Bergstrom, et al., *J. Appl. Phys.*, Vol. 36, pg. 693 (1974)). In addition, skeletal muscle B-NOS has a membrane location (in contrast to brain B-NOS) suggesting structural differences that might extend to the arginine-binding domain.

Figure 4B:
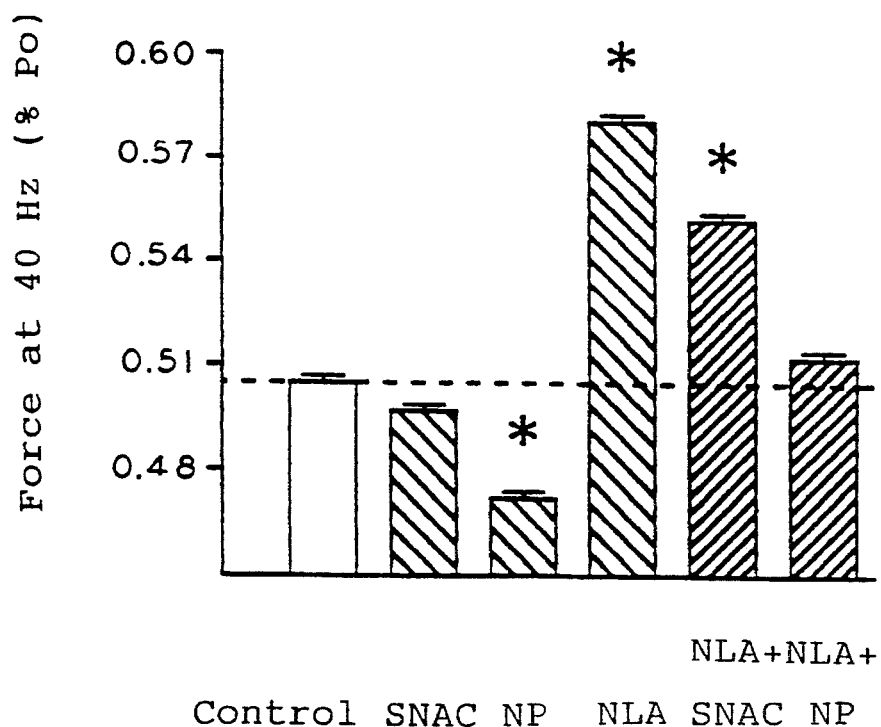

The findings that contractile function is sensitive to NO are further supported by additional observations. Hemoglobin, which traps NO, enhances force production during submaximal tetanic contraction (40 Hz) (50 uM, n=5, p=0.052; 50–250 uM, n=10, $p<0.001$). These effects are analogous to those seen in many other tissues where hemoglobin counteracts the effects of NO. Moreover, exogenous NO donors ((S-nitroso-N-acetylcysteine (SNAC) or nitroprusside (NP), 100 uM) produced the opposite effect, depressing contractile function. The effects of exogenous donors were exaggerated by NOS inhibition (FIG. 4b).

EXAMPLE 5

Role of Cyclic GMP

Figure 5:
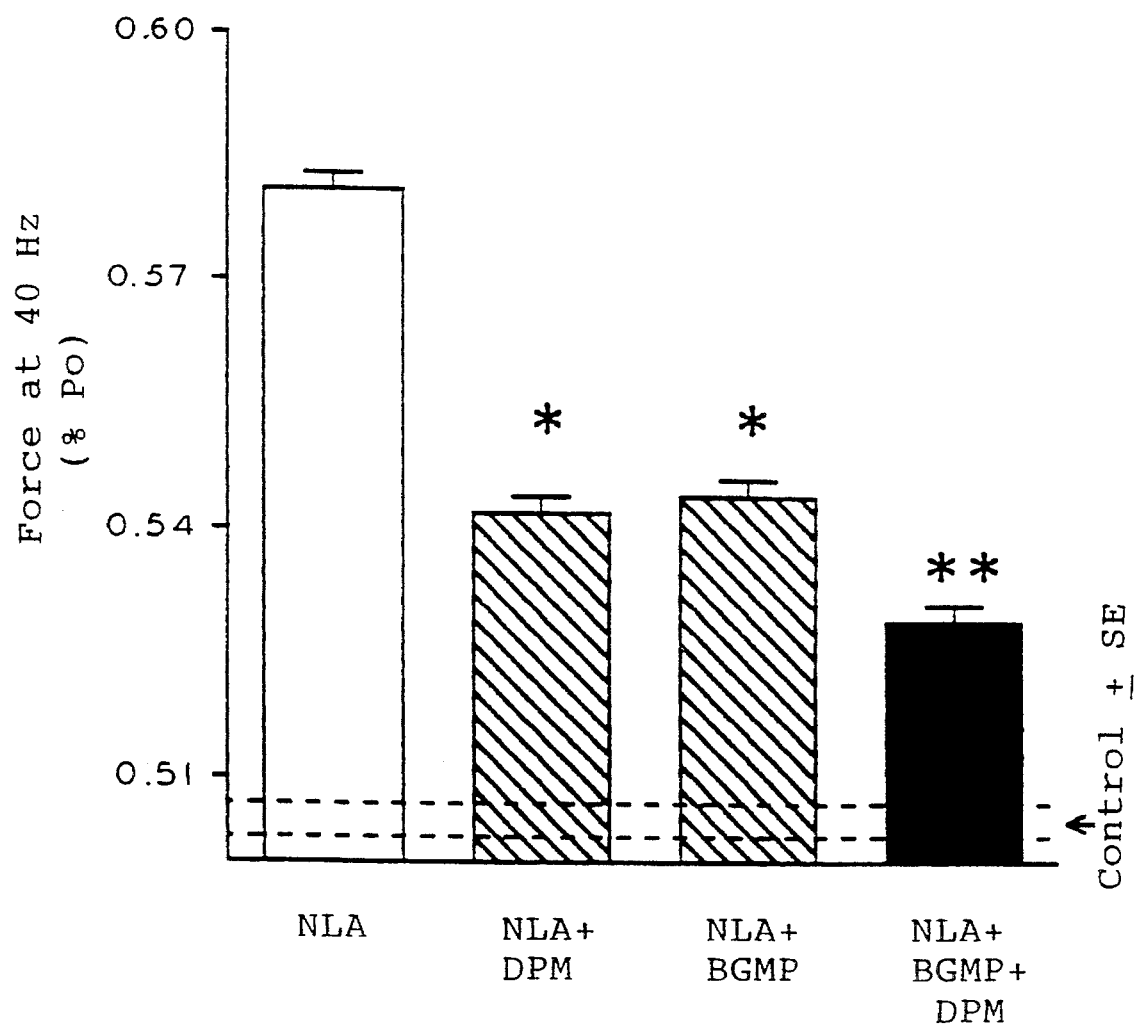
FIG. 5. cCGMP reverses contractile effects of NOS blockade. Fiber bundles were isolated from rat diaphragm and studied using methods described in the description of FIG. 3. Data are mean forces (±SE) developed at 40 Hz by fiber bundles (n=5 or 6/group) treated with NLA (transcribed from FIG. 4B), NLA plus dipyramidole (DPM; phosphodiesterase inhibitor) 10 uM, 8-bromo-cGMP (BGMP; exogenous CGMP analogue), or DPM plus BGMP. Forces are expressed as percentages of the average force developed at 40 Hz by time- and stimulus-matched control muscle (shown ±SE by horizontal dashed lines). All values were greater than control (p<0.0001). *=significantly different from NIA and from NLA+BGMP+DPM (p<0.0001); significantly different from all other groups (p<0.0001).

The data in FIG. 5 show that contractile increases caused by NOS inhibition are reversed by pharmacologic agents that increase CGMP levels including 8-bromo-cGMP (BGMP, a cell permeable CGMP analogue) and dipyridamole (DPM, a phosphodiesterase inhibitor). Greater inhibitory effects were seen with a combination of BGMP and dipyridamole ($p<0.0001$). These inhibitory effects are more striking in view of the potential increases in CAMP induced by dipyrimadole, that alone would be predicted to enhance the contraction of skeletal muscle (Westerblad, *Am. J. Physiol.*, Vol. 261, pg. C195 (1991)). In addition, methylene blue (10 uM), an agent that inhibits guanylate cyclase, increased force production during submaximal tetanic contraction ($p<0.001$) (data not shown). Measurements of CGMP by ELISA showed a reduction in levels to $85 \pm 11\%$ of control ($0.24 \pm 0.04$ pM/mg muscle, n=5) by NOS inhibition, that was reversed by the addition of NP to levels $47 \pm 28\%$ above control; these values, however, did not quite reach significance by ANOVA (p=0.13). Further supporting the importance of CGMP, immunohistochemical analysis using a CGMP specific monoclonal antibody (Casale, et al., *J. Cyclic. Nuc. Prot. Phosph. Res.*, Vol. 10, pg. 189 (1985)) confirmed the presence of CGMP in the area of the sarcolemma, placing it in the immediate vicinity of NOS (data not shown). These findings are consistent with the postulate that endogenous NO reversibly down regulates excitation-contraction coupling in skeletal muscle, and that NO acts, at least in part, via a cGMP-dependent mechanism. One possibility is that NO-stimulated cGMP production relieves phospholambin inhibition of the sarcoplasmic reticulum Ca2+-ATPase (Szymanska, et al., *Membr. Biochem.*, Vol. 9, pg. 191 (1990)).

EXAMPLE 6

Skeletal Muscle: NO, $O_2$— and Redox State

To study production of NO and $O_2$— by diaphragm bundles, the cytochrome c assay (Babior, et al., *J. Clin. Invest.*, Vol. 52, pg. 741 (1983)) was employed, which has been used to detect superoxide in skeletal muscle (Reid, et at., *J. Appl. Physiol.*, Vol. 73, pg. 1797 (1992)), and NO in bacteria. (Ehrenberg, *Acta Chem. Scand.* Vol. 14, pg. 1684 (1960); Kucera, et al., *Biochem. Biophys. Acta*, Vol. 894, pg. 120 (1987); Bell, et al., *Biochem. J.*, Vol. 273, pg. 423 (1991)). This assay showed that unfatigued muscle releases reducing equivalents (mean rate (±SE) of cytochrome c reduction=2.8±0.6 pM/mg muscle/min. at 37° C., n=25). Generation of reducing equivalents was blunted by NOS inhibition with NLA (Table 2), an effect abolished by the addition of NO donors to NLA-treated muscle (data not shown). In contrast, SOD and catalase did not affect basal production of reducing equivalents (Table 2). This contrasts sharply with results obtained from fatigued muscle in which cytochrome c reduction is increased 6-fold relative to passive muscle (p<0.001), 85 % of this increase being attributable to SOD-sensitive ROI (Table 2 below). These results indicate that reducing equivalents generated by unfatigued muscle are influenced by NO production (or that of a related redox form). Reduction of cytochrome c may result from the direct effect of NO (Ehrenberg, et al., 1960; Kucera, et al., 1987; Bell, et al., 1991) or from indirect effects on other enzymatic redox systems, for which there is precedent (Clancy, et al., *J. Clin. Invest.,* Vol. 90, pg. 1116 (1992)). Notwithstanding the precise mechanism, the production of NO under these conditions is supported by the several biochemical and functional studies reported above.

To obtain the data in Table 2 below, fiber bundles were isolated from rat diaphragm and incubated in oxygenated, buffered Krebs-Ringer solution containing cytochrome c, $5 \times 10^{-5}$M. After 60–90 min, solutions were removed and the absorbance at 550=was measured spectrophotometrically. Cytochrome c reduction rates (pmol/mg/min) were calculated and expressed relative to absorbance changes catalyzed by untreated (control) fiber bundles from the same muscle. Bath concentrations were NLA 1mM, SOD (superoxide dismutase) $10^3$ U/ml, catalase $10^3$ U/ml. Fatigue (used to assess effects during active contraction) was produced under isometric conditions using repetitive electrical field stimulation (supramaximal current density, 0.5 ms stimulus duration, 25 Hz, 250 ms train duration, 0.1 trains/s) for 1 hr. Differences from control: * P<0.05, ** P<0.001; difference from Fatigue: # P<0.001.

TABLE 2

| Treatment | Cytochrome C Reduction % Control ± SE |
|---|---|
| NLA | 67 ± 18* |
| SOD + Catalase | 106 ± 82 |
| Fatigue | 672 ± 83** |
| Fatigue + SOD | 188 ± 41# |

EXAMPLE 7

Oxyhemoglobin Improves Excitation-Contraction Coupling in Skeletal Muscle

We have shown that skeletal muscle produces nitric oxide (NO) and that endogenous NO depresses excitation-contraction coupling (Nature 372:546–548, 1994). We therefore postulated that oxyhemoglobin (an NO scavenger) should improve excitation-contraction coupling. Fiber bundles were isolated from rat diaphragm, mounted isometrically in Krebs-Ringer solution, and incubated at 37° C. for 1 hour before being alternately exposed to oxygenated hemoglobin (50–500 μM) or to Krebs-Ringer solution (control) at 18 minute intervals. Direct electrical stimulation ((0.2) ms pulses, 250 ms trains, supramaximal voltage) was used to produce submaximal (40 Hz) and maximal (200 Hz) tetanic contractions. Developed force was measured. Oxyhemoglobin produced dose-dependent increases in relative force (as % Po) developed during submaximal tetanic contractions (p<0.05). Maximal tetanic stress (Po, in $N/cm^2$) was acutely depressed by oxyhemoglobin exposure (p<0.05 for 50 μM and 250 μM concentrations). All oxyhemoglobin effects reversed with washout. We conclude that oxyhemoglobin improves excitation-contraction coupling and also causes reversible depression of Po.

It is to be understood, however, that the scope of the present invention is not to be limited to the specific embodiments described above. The invention may be practiced other than as particularly described and still be within the scope of the accompanying claims.

What is claimed is:

1. A method for treating a mammal by stimulating the contraction of skeletal muscle of said mammal comprising: treating a mammal in need of treatment for amyotrophic lateral sclerosis, muscular dystrophies, congestive heart failure, or lung diseases by contraction of skeletal muscle by administering to said mammal a skeletal muscle contracting amount of a nitric oxide synthase inhibitor.

2. The method of claim 1 wherein said nitric oxide synthase inhibitor is selected from the group consisting of $N^G$-monomethyl-L-arginine; nitroarginine; N-nitro-L-arginine methyl ester; N-amino-L-arginine; N-methyl-L-arginine; ornithine; N-imino-ethyl-L-ornithine; methylene blue; trifluoropiperazine; heme binders; and methotrexate.

3. A process for enhancing skeletal muscle contraction in a mammal in need thereof comprising: treating the mammal in need of skeletal muscle contraction enhancement with an amount of a heme-containing compound effective to enhance skeletal muscle contraction in said mammal.

4. A method for stimulating the contraction of skeletal muscle in a mammal in need thereof comprising administering to said mammal in need thereof a skeletal muscle contraction enhancing amount of a nitric oxide scavenger.

5. The method of claim 4 wherein the nitric oxide scavenger is a heme-containing compound.

6. The method of claim 5 wherein the heme-containing compound is a heme-containing protein.

7. The method of claim 6 wherein the heme-containing protein is selected from the group consisting of hemoglobin and myoglobin.

* * * * *